United States Patent [19]

Schumann

[11] Patent Number: Plant 5,374

[45] Date of Patent: Dec. 18, 1984

[54] GERANIUM PLANT NAMED SCHÖNE HELENA

[75] Inventor: Ingeborg Schumann, Bad Ems, Fed. Rep. of Germany

[73] Assignee: Pelargonien-Fischer KG, Hillscheid, Fed. Rep. of Germany

[21] Appl. No.: 548,222

[22] Filed: Nov. 2, 1983

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of geranium named Schöne Helena particularly characterized by the combined features of porcelain rose flower color, large flowerhead, very fast rooting, cultivation below 12° C., excellent branching, medium to dark green foliage, and stable peduncles.

3 Drawing Figures

The present invention comprises a new and distinct cultivar of geranium, botanically known as *Pelargonium zonale,* and hereinafter referred to by the cultivar name Schöne Helena.

Schöne Helena is a product of planned breeding program which had the objective of creating new geranium cultivars with salmon flower color, semi-double flower form, short plant height, fast rooting, good branching, and durable flowers.

Schöne Helena was originated from a hybridization made in a controlled breeding program in Hillscheid, Federal Republic of Germany in 1979. The female parent was an unpatented cultivar named Tany having porcelain rose color semi-double flowers, but inferior branching characteristics. The male parent of Schöne Helena was the unpatented cultivar PAC® Lachsball, principally characterized by its salmon semi-double flowers, lack of zonation in the foliage, compact habit, and fast rooting.

Schöne Helena was discovered and selected as one flowering plant within the progeny of the stated cross by Ingeborg Schumann on June 27, 1980 in a controlled environment in Hillscheid, Federal Republic of Germany.

The first act of asexual reproduction of Schöne Helena was accomplished when vegetative cuttings were taken from the initial selection in January, 1981 in a controlled environment in Hillscheid, Federal Republic of Germany by a technician working under formulations established and supervised by Ingeborg Schumann. Horticultural examination of selected units initiated in the Spring of 1981 and continuing in 1982 has demonstrated that the combination of characteristics as herein disclosed for Schöne Helena are firmly fixed and are retained through successive generations of asexual reproduction.

Schöne Helena has not been observed under all possible environmental conditions. The phenotype may vary significantly with variations in environment such as temperature, light intensity, and day length. The following observations, measurements, and comparisons describe plants grown in Hillscheid, Federal Republic of Germany under greenhouse conditions which approximate those generally used in commercial practice.

The following traits have been repeatedly observed and are determined to be basic characteristics of Schöne Helena which in combination distinguish this geranium as a new and distinct cultivar:

1. Porcelain rose flower color.
2. Large flowerhead (umbel).
3. Zoned leaves.
4. Very fast rooting.
5. Schöne Helena can be cultivated below 12° C.
6. EXcellent branching, producing an average of 4.2 branches per plant.
7. Medium to dark green foliage color.
8. Stable peduncles.
9. Chlorophyll quality excellent for transportation.

Of the many commercial cultivars known to the present inventor, the most similar in comparison to Schöne Helena are the unpatented cultivars Salmon Irene and Springtime Irene. Reference is made to attached Chart A which compares certain characteristics of Schöne Helena to those same characteristics of Salmon Irene and Springtime Irene. In general comparison to Salmon Irene, Schöne Helena has faster rooting, better branching, shorter internode length, and shorter plant height. In comparison to Springtime Irene, Schöne Helena has smaller leaves, lighter flower color, better weather resistance, better branching, and faster rooting.

The accompanying photographic drawings show typical flower and foliage characteristics of Schöne Helena, with colors being as true as possible will illustrations of this type. Sheet 1 is a perspective view of a potted plant of the new cultivar. Sheet 2 is a relatively enlarged view of the flowers, buds and foliage, and sheet 3 is a black and white print of the underside of typical foliage of the new cultivar.

In the following description color references are made to The Royal Horticultural Society Color Chart, except where additional or alternative values from Horticultural Color Chart (H.C.C.) are indicated. The color values were determined between 3:40 and 3:50 P.M. on Aug. 12, 1983 under 20,000 Klux at Hillscheid, Federal Republic of Germany.

CLASSIFICATION

Botanical: A hybrid of the genus *Pelargonium l'hert.*
Commercial: Schöne Helena.

INFLORESCENCE

Umbel:

*Average diameter.*—122 mm.
*Average depth.*—81 mm.
*Peduncle length.*—200 mm.
*Pedicel length.*—26 mm. (without anthocyan).

Corolla:
*Average diameter.*—45 mm.
*Form.*—Semi-double, rotate.
*Color (general tonality from a distance of three meters).*—H.C.C. 619/1, R.H.S. 38A.
*Color (abaxial).*—H.C.C. 620/1, R.H.S. 44D.
*Color (adaxial).*—H.C.C. 620/2.

Bud:
*Shape.*—Elliptic.
*Color (abaxial).*—Pink to nearly white.

Reproductive organs:
*Androecium.*—Monodelphous; 8 stamens; plentiful pollen.
*Gynoecium.*—4-6 lobed stigma, color rose; style, color rose.

Spring flowering response period: In Hillscheid, Federal Republic of Germany in 1982, 40% of plants with at least 1 flower opened 13 weeks after planting of unrooted cutting.

Outdoor flower production: The flower count in 1982 in Hillscheid, Federal Republic of Germany was between 44 and 49 flowers per plant for June through October observation period.

Durability: Shatter resistance very good.

PLANT

Foliage:
*Form.*—Kidney-shaped.
*Margin.*—Crenate.
*Color (abaxial).*—Medium to dark green.
*Color (adaxial).*—Medium green.
*Color (zonation).*—Brown.

*Tolerance to botrytis.*—Good.

General appearance and form:
*Internode length.*—36 mm.
*Branching pattern.*—Good, with an average of 4.2 branches per plant being produced.
*Height.*—290 mm.; medium.

CHART A

| | Branching Habit (number of branches of non-pinched plants 13 weeks after planting unrooted cutting) | Corolla Color | Hillscheid Spring Flowering Response | Internode Length |
|---|---|---|---|---|
| Springtime Irene | 3.3 | RHS 52D | 35% (late) | medium |
| Salmon Irene | 3.0 | RHS 44D | 50% (early) | long |
| Schone Helena | 4.2 | RHS 44D | 40% (midseason) | medium |

| | Plant Height | Color of Leave | Quality of Chorophyll for Transportation | Rooting Time |
|---|---|---|---|---|
| Springtime Irene | medium | light-green | bad | medium |
| Salmon Irene | tall | middle-green | good | slow |
| Schone Helena | medium | middle-green | very good | very fast |

I claim:

1. A new and distinct cultivar of geranium named Schöne Helena, as described and illustrated, and particularly characterized by the combined features of porcelain rose flower color, large flowerhead, very fast rooting, cultivation below 12° C., excellent branching, medium to dark green foliage, and stable peduncles.

* * * * *

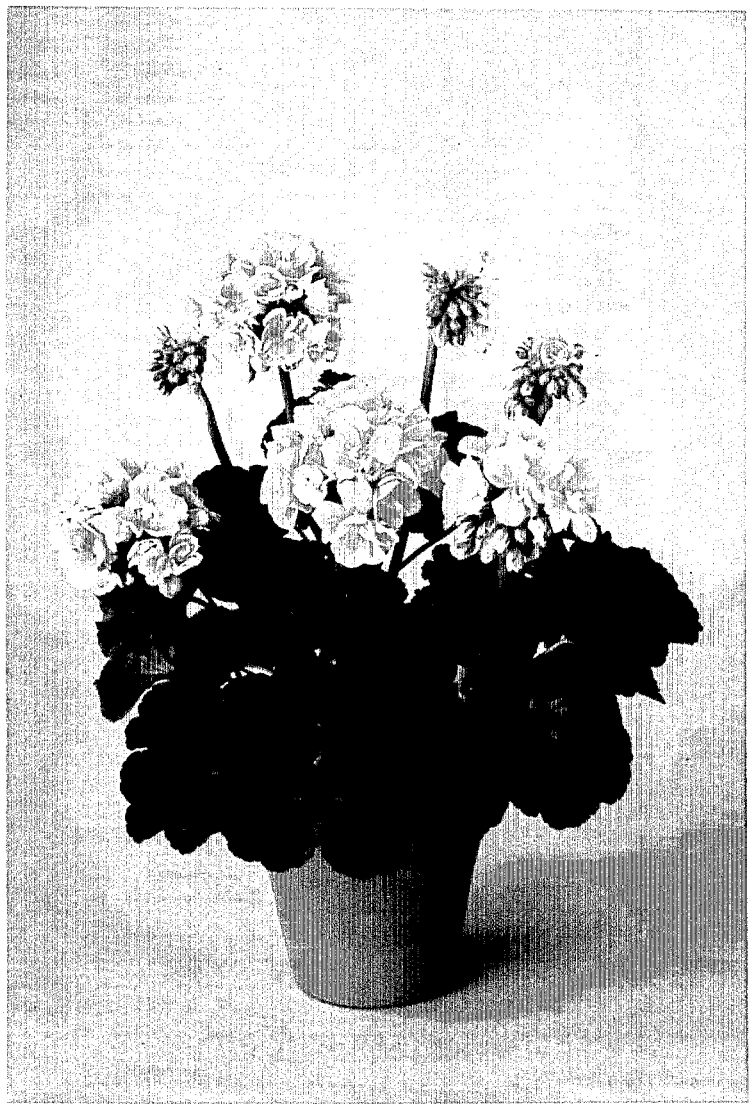

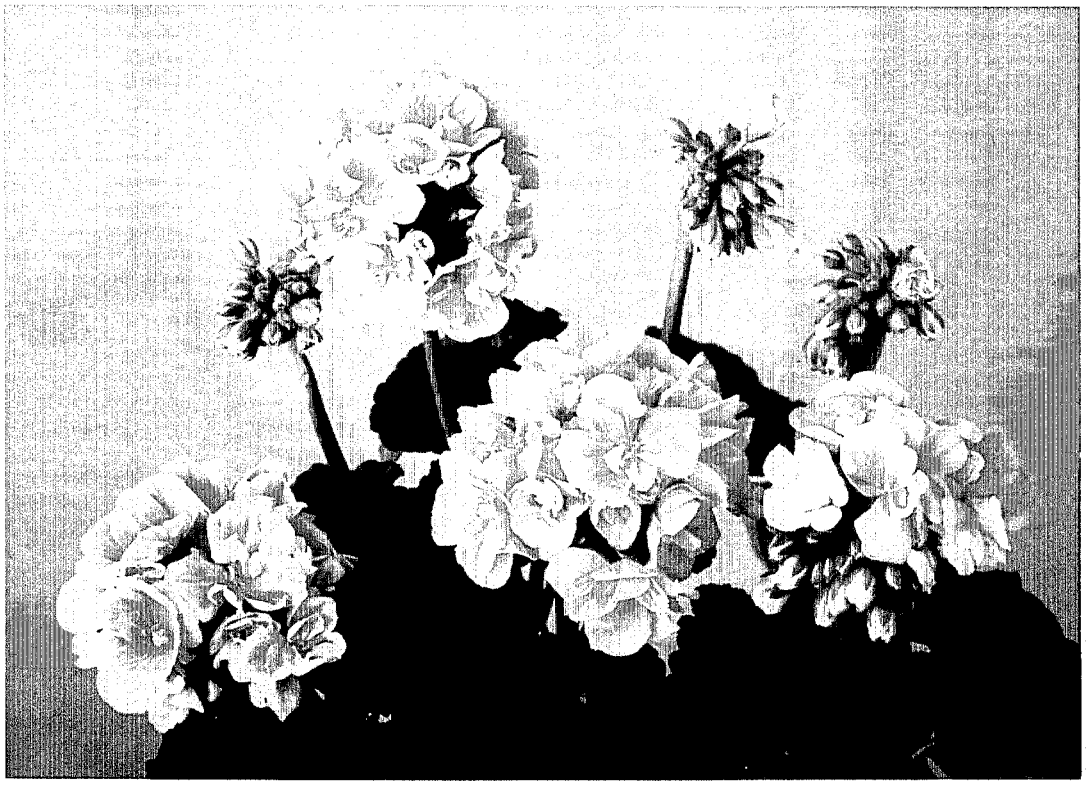

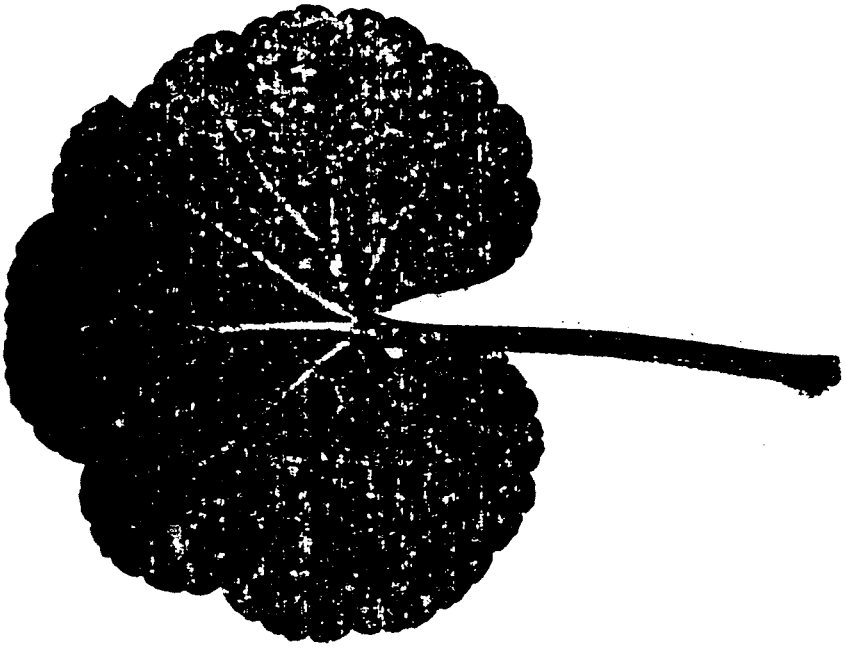
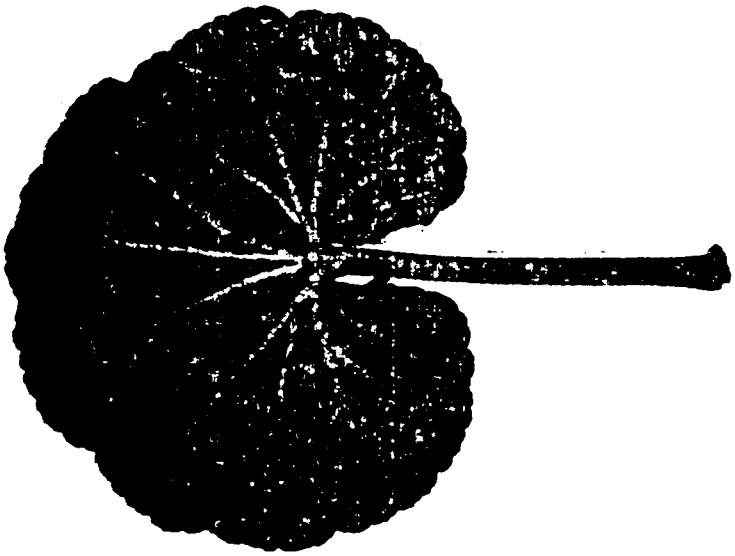

Schöne Helena